United States Patent [19]

Conner et al.

[11] Patent Number: 4,457,911

[45] Date of Patent: Jul. 3, 1984

[54] DIALKYL MALONATES AS ORGANIC SUNSCREEN ADJUVANTS

[75] Inventors: Donald E. Conner, Clifton; Boris M. Cumpelik, Hillsdale, both of N.J.

[73] Assignee: Van Dyk & Company Inc., Belleville, N.J.

[21] Appl. No.: 404,964

[22] Filed: Aug. 3, 1982

Related U.S. Application Data

[63] Continuation-in-part of Ser. No. 229,383, Jan. 28, 1981, abandoned.

[51] Int. Cl.$^3$ ............................ A61K 7/42; A61K 7/44
[52] U.S. Cl. ............................................ 424/59; 424/60
[58] Field of Search .............................. 424/59, 60, 308

[56] References Cited

U.S. PATENT DOCUMENTS

| | | | |
|---|---|---|---|
| 3,123,647 | 3/1964 | Duennenberger et al. | 424/59 X |
| 3,160,665 | 12/1964 | Siegrist et al. | 424/59 X |
| 3,415,875 | 12/1968 | Luethi et al. | 424/59 X |
| 3,670,074 | 6/1972 | Doner | 424/59 |
| 3,895,104 | 7/1975 | Karg | 424/60 |

FOREIGN PATENT DOCUMENTS

| | | | |
|---|---|---|---|
| 110554 | 8/1956 | Fed. Rep. of Germany | 424/59 |
| 1087902 | 8/1960 | Fed. Rep. of Germany | 424/59 |
| 2604554 | 8/1977 | Fed. Rep. of Germany | 424/59 |
| 39660 | 3/1977 | Japan | 424/308 |

*Primary Examiner*—Dale R. Ore
*Attorney, Agent, or Firm*—L. Chasan

[57] ABSTRACT

Compositions containing an organic sunscreen and particular substituted dialkyl malonates adjuvants therefor are very effective in providing broad spectrum sunscreen protection.

9 Claims, No Drawings

DIALKYL MALONATES AS ORGANIC SUNSCREEN ADJUVANTS

CROSS REFERENCE TO RELATED APPLICATIONS

This application is a continuation-in-part of Ser. No. 229,383 filed Jan. 28, 1981, now abandoned.

FIELD OF THE INVENTION

Extensive studies have been made of the ultraviolet radiation of sunlight and skylight reaching the surface of the earth and the effects of such radiation on the human skin. It has been established that the radiation between 290 nanometers and 315 nanometers produces substantially all of the burning, or erythemal energy, and a substantial portion of the tanning energy, while the between 315 nanometers and 400 nanometers promotes incident tanning. The cosmetic industry has divided these spectra into respectively UV-B, and UV-A. The different intensities and the erythemal and tanning effectiveness of the various wave lengths within these ranges have been established and methods have been determined for calculating accurately their effects on normal untanned skin.

Approximately 76% of the physiological tanning potential of sunlight is found in the ultraviolet range between 290 nanometers and 315 nanometers, the so-called UV-B or erythema area; the balance is found in the range between 315 nanometers and 400 nanometers, the so-called UV-A tanning area.

Typical organic sunscreens such as 2-ethylhexyl para methoxy cinnamate, homomenthyl salicylate, p-aminobenzoic acid and its esters, p-dimethyl amino benzoates, hydroxy and dihydroxy-4-methoxy benzophenones, oxybenzone, and dioxybenzone, provide protection in the erythemal UV-B area, but lesser protection in the tanning area.

It is becoming increasingly apparent that ultraviolet in the tanning UV-A area can also have detrimental effects on skin health, e.g. causing premature aging as well as skin cancer. Accordingly, the need has developed for more effective broad spectrum sun screens to filter out the entire radiation. This need can mean disrupting established formulation procedures, with the usual cosmetic oil carriers.

PRIOR ART

Some malonates have been disclosed as UV absorbers for industrial uses. Typically they are completely unsuitable for cosmetic purpose in human applications, e.g. German Pat. No. 1,087,902. A malonate, diethyl p-dimethyl-aminobenzalmalonate has been disclosed in U.S. Pat. No. 3,895,104 as a conventional UV absorber in a polyamide resin film, but actually provides substantially no protection, even in the burning range.

SUMMARY OF THE INVENTION

It has now been found that particular substituted dialkyl malonates provide surprising protection in the tanning area, particularly around 370 nanometers, and are compatible with and adjuvants for organic sunscreens. This permits of utilizing established formulation procedures.

DETAILED DESCRIPTION OF THE INVENTION

The adjuvants of this invention are substituted dialkyl malonates in which the R alkyl group has from 1 to 5 carbon atoms as illustrated in the following moiety:

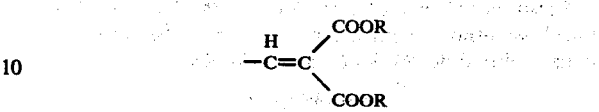

The efficacy of the dialkyl malonates as adjuvants are determined in an empiric manner. Thus the particularly preferred compounds are p-methoxy benzal diethyl malonate, p-methoxy benzal diisobutyl malonate, cinnamal diethyl malonate, indolal diethyl malonate, fural diethyl malonate, and 3,4,5 trimethoxy benzal diethyl malonate. The cinnamal compound is especially effective.

The adjuvants of this invention are prepared by a typical Knoevenagel reaction.

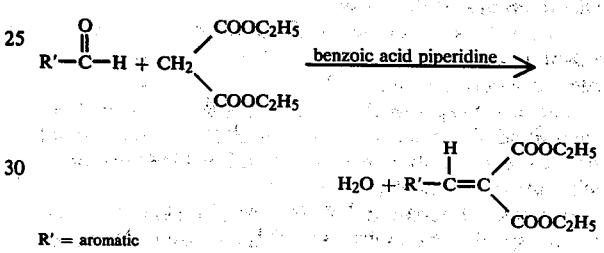

R' = aromatic

The solids are crystallized from e.g. isopropanol and the liquids are fractionately distilled off under vacuum.

The organic sunscreens with which the adjuvants of this invention are employed are discussed above. A benzalphthalide may also be used, U.S. Pat. No. 4,333,920, particularly 4-pentoxybenzalphthalide.

The overall composition adapted for application to the human skin thus comprises a cosmetic oil carrier known to the trade, e.g. mineral, vegetable and animal oils and isopropyl myristate, with an organic sunscreen, and an adjuvant of this invention. The sunscreen and the adjuvant are utilized in an amount sufficient to provide the desired protection for the skin. Typical total amounts of sunscreens and adjuvants comprise up to about 10 wt.% of the composition.

This invention, product workup and properties of the composition will be better understood by reference to the following examples.

EXAMPLE 1

A mixture containing 35% 2,2-dihydroxy-4-methoxy benzophenone and 65% cinnamal diethyl malonate produced a total block when used at a concentration of between 5% to 10% in the final composition.

EXAMPLE 2

Between 5%–6% of a mixture containing 50% 2-ethylhexyl-p-dimethylamino benzoate and 50% diethyl cinnamal malonate produced a total block.

EXAMPLE 3

Between 5%–5.5% of a mixture containing 50% 2-ethylhexyl-p-methoxy cinnamate and 50% diethyl cinnamal malonate produced a total block.

EXAMPLE 4

Between 4.5%-5% of a mixture containing 25% 4-pentoxy benzalphthalide and 75% diethyl p-methoxy benzal malonate produced a total block.

EXAMPLE 5

Between 5%-6% of a mixture containing 30% diisobutyl p-methoxy benzal malonate and 70% 4-pentoxy benzal phthalide produced a total block.

EXAMPLE 6

Between 3%-4% of a mixture containing 50% p-methoxy benzal phthalide and 50% diethyl fural malonate produced a total block.

Other formulations according to this invention provide similar results.

Substituted derivatives of the adjuvants of this invention can be employed, particularly of the cinnamal diethyl malonate.

These examples demonstrate that the materials of this invention in even small quantities are extremely effective adjuvants for organic sunscreens and remedy the shortcomings of the latter.

As can be seen, mixtures of the materials of this invention, and also the organic sunscreens, can be employed where desired.

The advantages of this invention will be apparent to the skilled in the art. Improved, highly effective, novel broad spectrum sunscreen compositions are made available, utilizing a dialkyl malonate.

It will be understood that this invention is not limited to the specific examples which have been offered as particular embodiments, and that modifications can be made without departing from the spirit thereof.

What is claimed is:

1. A composition adapted for application to the human skin comprising a cosmetic oil carrier containing distributed therein an effective amount to provide substantial protection against erythemal and tanning radiation of an organic sunscreen selected from the group consisting of 2-ethylhexyl para methoxy cinnamate, homomenthyl salicylate, p-amino-benzoic acid and its esters, p-dimethyl amino benzoates, hydroxy and dihydroxy-4-methoxy benzophenones, and a benzalphthalide, and as an adjuvant therefor a dialkyl malonate selected from the group consisting of p-methoxy benzal diethyl malonate, p-methoxy benzal diisobutyl malonate, cinnamal diethyl malonate, indolal diethyl malonate, fural diethyl malonate, and 3,4,5 trimethoxy benzal diethyl malonate.

2. The composition of claim 1 in which the adjuvant is p-methoxy diisobutyl malonate.

3. The composition of claim 1 in which the adjuvant in cinnamal diethyl malonate.

4. The composition of claim 1 in which the organic sunscreen is 4-pentoxybenzalphthalide.

5. A method of protecting the human skin from the effects of erythema and tanning radiation in sunlight which comprises applying to said skin an effective sunscreening amount of an organic sunscreen selected from the group consisting of 2-ethylhexyl para methoxy cinnamate, homomenthyl salicylate, p-amino-benzoic acid and its esters, p-dimethylamino benzoates, hydroxy and dihydroxy-4-methoxybenzophenones, and a benzalphthalide, and as an adjuvant therefor a dialkyl malonate selected from the group consisting of p-methoxy benzal diethyl malonate, p-methoxy benzal diisobutyl malonate, cinnamal diethyl malonate, indolal diethyl malonate, fural diethyl malonate, and 3,4,5 trimethoxy benzal diethyl malonate.

6. The method of claim 5 in which the adjuvant is p-methoxy benzal diisobutyl malonate.

7. The method of claim 5 in which the adjuvant is cinnamal diethyl malonate.

8. The method of claim 5 in which the organic sunscreen is 4-pentoxybenzalphthalide.

9. The composition of claim 3 in which the total amount of sunscreen and adjuvant comprise up to about 10 wt.% of the composition.

* * * * *